United States Patent [19]
Sommer et al.

[11] 3,956,365
[45] May 11, 1976

[54] HALOALKYL-CARBAMOXYALKYL DERIVATIVES

[75] Inventors: Harold Z. Sommer, Havre de Grace; Jacob I. Miller, Baltimore, both of Md.

[73] Assignee: The United States of America as represented by the Secretary of the Army, Washington, D.C.

[22] Filed: Feb. 28, 1967

[21] Appl. No.: 619,481

Related U.S. Application Data
[62] Division of Ser. No. 574,497, Aug. 18, 1966.

[52] U.S. Cl. ............................................ 260/482 C
[51] Int. Cl.² ...................................... C07C 125/06
[58] Field of Search ................................ 260/482 C

[56] References Cited
OTHER PUBLICATIONS
Adams et al., Chem. Reviews, Vol. 65, pp. 569 to 571, (1965).

*Primary Examiner*—Leland A. Sebastian
*Attorney, Agent, or Firm*—Nathan Edelberg; Robert P. Gibson; Kenneth P. VanWyck

[57] ABSTRACT

New chemical compounds which are useful as chemical warfare agents and as compounds to produce other incapacitating agents, said new compounds having the formula:

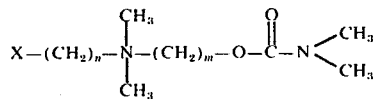

where $m$ is 2 to 6, $n$ is 6 to 16, and where X is a halogen selected from the group consisting of chlorine, bromine, and iodine.

3 Claims, No Drawings

HALOALKYL-CARBAMOXYALKYL DERIVATIVES

This application is a divisional application of my pending U.S. patent application Ser. No. 574,497 filed Aug. 18, 1966.

This invention relates to the synthesis of new chemical compounds that are useful as chemical warfare agents. More particularly, our invention is concerned with novel quaternary incapacitating and potential otherwise physiologically active compounds.

The chemical agents act mostly on the peripheral autonomic cholinergic nervous system which includes the motor nerves, all preganglionic fibers and the postganglionic parasympathetic fibers. The transmission of impulses along a nerve or from nerve fibers to muscle fibers or secretory cells or from one nerve fiber to another across synapses in ganglia is thought to involve chemical changes either directly or as the source of potential differences. Our chemical agents interfere with the normal process of neuromuscular impulse transmission and thus modify or disrupt the propogation of impulses from nerves to muscles. We have also found these compounds to produce incapacitation effects, such as decreased locomotion activity, tremors, decreased respiratory rate at relatively low dose levels in various animals.

The object of this invention is to synthesize new incapacitating agents in high yields wherein said products are well suited for industrial scale manufacture.

Other objects of and uses for the invention will in part be obvious and will in part appear hereinafter in the following detailed description thereof.

Our compounds are useful as chemical warfare agents and as potential otherwise physiologically active materials.

Our compounds may be employed in any munition suitable for handling a relatively non-volatile toxic agent such as bombs, shells, spray tanks, rockets, missiles, aerosol generators, and others.

In accordance with our invention, a ω-haloalkyl-carbamoxyalkyl-dimethylammonium halide and 3-quinuclidinol were dissolved in a ketone and the solution was allowed to stand for several hours at room temperature. The ketone was decanted from the oily material which formed. An alcohol was added to the oily material, the resultant solution was treated with charcoal and evaporated. The oily residue became crystalline after it was triturated with a liquid ketone and the product was collected and dried.

The new compounds of our invention may be represented by the following generic formula:

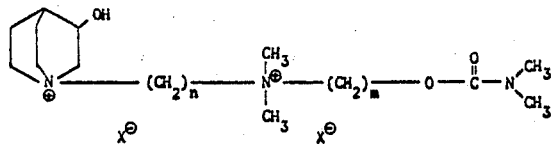

where $m$ is 2 to 6, $n$ is 6 to 16, and where $^-$ is one equivalent of a non-toxic monovalent or polyvalent anion.

The procedure used for the preparation of the new toxic materials is schematically shown as follows:

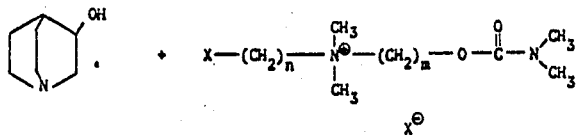

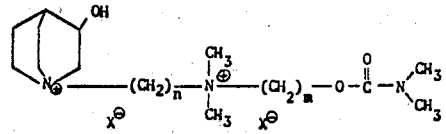

where $m$ and $n$ are the same as above, X is a halide radical and $^-$ is the corresponding halide anion, preferably chlorine, bromine, or iodine.

If compounds are desired in which X is other than a halide ion, the above compounds are treated with the desired acid by a simple exchange reaction as set forth below.

The starting material, 3-quinuclidinol, is commercially available, the ω-haloalkyl-carbamoxyalkyl-dimethylammonium halides were synthesized by the sequence of reactions schematically shown below:

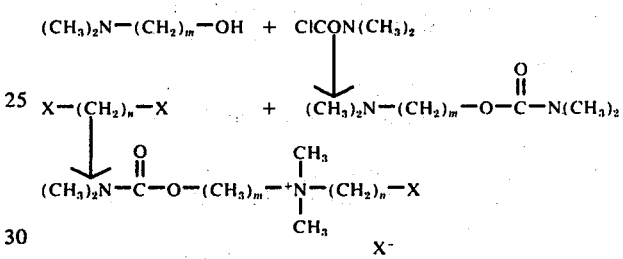

where $m$, $n$, and X are the same as above.

PREPARATION 1

A mixture of 2-dimethylaminoethanol (22.3g.), dimethylcarbamoyl chloride (12.5g.), and benzene (150 ml) was refluxed for 17 hours and then cooled to room temperature. The benzene solution was decanted from the precipitate that formed during the reaction and distilled under reduced pressure. 2-dimethylcarbamoxyethyldimethylamine (17g.), boiling between 133°–135°C at 50mm pressure, was collected and dissolved in 350 ml of acetone. 1,10 dibromodecane (95g.) was added and the solution was allowed to stand at room temperature for three days. The precipitate that formed was removed by filtration. Diethyl/ether (Ca, 3 liters) was added to the filtrate, causing the desired 10-bromodecyl (2-dimethylcarbamoxyethyl)-dimethylammonium bromide to precipitate. The white crystalline material (29.5g.) was collected on a filter and dried, m.p. 87°–89°C.

Anal. Calcd. for $C_{17}H_{36}Br_2N_2O_2$: C, 44.4; H, 7.8; Br, 34.8. Found: C, 44.3; H, 7.7; Br, 34.7.

EXAMPLE 1

10-Bromodecyl(2-dimethylcarbamoxyethyl)dimethylammonium bromide (1.5g.) and 1.5g. of 3-quinuclidinol were dissolved in 100 ml of acetone and the solution was allowed to stand for 16 hours at room temperature. After decanting the acetone from the oily layer which had separated, the oil was dissolved in 30 ml of ethanol. After treatment with charcoal and evaporation of the solvent, ethyl acetate was added to the oily residue. The oil crystallized after allowing the mixture to stand at room temperature overnight. The white crystalline product, decamethylene-(3-hydroxyquinuclidinium bromide)[(2-dimethylcarbamoxyethyl)dimethylammonium bromide], was collected and dried. The compound (0.84g.) melted at 141°–142°C.

Anal. Calcd. for $C_{24}H_{49}N_3O_3Br_2$: C, 49.1; H, 8.35; Br, 27.25

Found: C, 49.0; H, 8.4; Br, 26.9.

| Iv MED$_{50}$ | in mice | 0.056 mg/kg |
|---|---|---|
| Iv LD$_{50}$ | in mice | 0.560 mg/kg |

$$\frac{LD_{50}}{MED_{50}} = 10$$

The compounds listed below, which are representative of our invention can be prepared by the above techniques using the appropriate starting materials.

Decamethylene-(3-hydroxyquinuclidinium-bromide)[(2-dimethylcarbamoxyethyl)dimethylammoniumbromide].

Decamethylene-(3-hydroxyquinuclidinium-bromide)[(3-dimethylcarbamoxypropyl)dimethylammoniumbromide].

Decamethylene-(3-hydroxyquinuclidinium-bromide)[(4-dimethylcarbamoxybutyl)dimethylammoniumbromide].

Decamethylene-(3-hydroxyquinuclidinium-bromide)[(5-dimethylcarbamoxypentyl)dimethylammoniumbromide].

Decamethylene-(3-hydroxyquinuclidinium-bromide)[(6-dimethylcarbamoxyhexyl)dimethylammoniumbromide].

Octamethylene-(3-hydroxyquinuclidinium-bromide)[(2-dimethylcarbamoxyethyl)dimethylammoniumbromide].

Octamethylene-(3-hydroxyquinuclidinium-bromide)[(3-dimethylcarbamoxypropyl)dimethylammoniumbromide].

Dodecamethylene-(3-hydroxyquinuclidinium-bromide)[(2-dimethylcarbamoxyethyl)dimethylammoniumbromide].

Dodecamethylene-(3-hydroxyquinuclidinium-bromide)[(3-dimethylcarbamoxypropyl)dimethylammoniumbromide].

Hexadecamethylene-(3-hydroxyquinuclidinium-bromide)[(2-dimethylcarbamoxyethyl)dimethylammoniumbromide].

Hexadecamethylene-(3-hydroxyquinuclidinium-bromide)[(3-dimethylcarbamoxypropyl)dimethylammoniumbromide].

We have shown a preferred compound in which the anion is limited to the halogen moiety, in particular the bromide, since the bromoalkanes are readily available and are good quaternizing agents. In general, however, it is only necessary that the anions merely have to meet the requirement of being capable of forming a stable salt with the quaternary nitrogen. Thus, the halogen ions can be exchanged with other anions of a relatively strong monovalent or polyvalent acid by conventional methods. For example, if X is a bromide in the final product, a solution of the compound can be treated with a basic ion exchange resin or mixed with silver oxide and, subsequently, the desired acid is added to the quaternary hydroxide solution. Anions other than the halogens may be supplied directly or by metathesis with the halide form of the quaternary ammonium compound. Also suitable as representations of $X^-$ are the anions hydrogen sulfate, nitrate, hydrogen oxalate, perchlorate, and tetraphenylboronate. Representative examples of these additional monovalent or polyvalent end products are:

Decamethylene-(3-hydroxyquinuclidinium hydrogen sulfate) [(2-dimethylcarbamoxyethyl)dimethylammonium hydrogen sulfate]. [Decamethylene-(3-hydroxyquinuclidinium nitrate)[(2-dmethylcarbamoxyethyl)dmethylammonium nirate].

Decamethylene-(3-hydroxyquinuclidinium perchlorate)[(3-dimethylcarbamoxypropyl)dimethylammonium perchlorate].

Decamethylene-(3-hydroxyquinuclidinium tetraphenylboronate) [(3dmethylcarbamoxypropyl)dimethylamonium tetraphenylboronate].

Decamethylene-(3-hydroxyquinuclidinium hydrogen oxalate) [(4-dimethylcarbamoxybutyl)dmethylammonium hydrogen oxalate].

We claim:

1. Compounds having the formula:

$$X-(CH_2)_n-N(CH_3)_2-(CH_2)_m-O-C(=O)-N(CH_3)_2$$

where $m$ is 2 to 6, $n$ is 6 to 16, and where X is a halogen selected from the group consisting of chlorine, bromine, and iodine.

2. 10-bromodecyl(2-dimethylcarbamoxyethyl)dimethylammonium bromide.

3. 10-bromodecyl(3-dimethylcarbamoxypropyl)dimethylammonium bromide.

* * * * *